(12) United States Patent
Stack et al.

(10) Patent No.: US 11,364,377 B2
(45) Date of Patent: Jun. 21, 2022

(54) INSTRUMENT FOR FACILITATING TRANSSEPTAL DELIVERY OF CARDIAC THERAPEUTIC DEVICES

(71) Applicant: Synecor LLC, Chapel Hill, NC (US)

(72) Inventors: Richard S Stack, Chapel Hill, NC (US); William L Athas, Chapel Hill, NC (US); Kevin Johnson, Durham, NC (US); Emer M Feerick, Galway (IE); Matthew Moran, Galway (IE); Damian Muldoon, Galway (IE); Liam Ruddy, Mayo (IE)

(73) Assignee: SYNECOR LLC, Durham, NC (US)

( * ) Notice: Subject to any disclaimer, the term of this patent is extended or adjusted under 35 U.S.C. 154(b) by 0 days.

(21) Appl. No.: 16/578,379

(22) Filed: Sep. 22, 2019

(65) Prior Publication Data
US 2020/0253635 A1 Aug. 13, 2020

Related U.S. Application Data

(60) Provisional application No. 62/802,212, filed on Feb. 7, 2019.

(51) Int. Cl.
*A61M 60/857* (2021.01)
*A61B 17/34* (2006.01)
(Continued)

(52) U.S. Cl.
CPC ....... *A61M 60/857* (2021.01); *A61B 17/3468* (2013.01); *A61F 2/2427* (2013.01);
(Continued)

(58) Field of Classification Search
CPC .......... A61M 25/0136; A61M 25/0147; A61M 2025/015; A61M 1/1008; A61M 1/122;
(Continued)

(56) References Cited

U.S. PATENT DOCUMENTS 5,190,050 A    3/1993    Nitzsche
5,285,795 A *   2/1994    Ryan ................ A61B 17/32002
                                                                     600/562
(Continued)

FOREIGN PATENT DOCUMENTS

EP      1534374 B1    1/2007
EP      1807143 A1    7/2007
(Continued)

OTHER PUBLICATIONS

Sondergaard, Lars et al, First-in-Human Case of Transfemoral CardiAQ Mitral Valve Implantation, Circ. Cardiovasc Interv. 2015.
(Continued)

*Primary Examiner* — Katherine H Schwiker

(57) ABSTRACT

An instrument for facilitating transseptal delivery of a cardiac therapeutic device is positionable in a left ventricle. The instrument includes an elongate shaft having a tubular lumen, the shaft having a proximal portion and a distal portion actively steerable between a generally straight position and a curved position. An external pull wire and an internal pull wire are each actuatable to move the distal portion to the curved position. The external pull wire extends internally through the proximal portion of the shaft and longitudinally along the exterior of the distal portion of the shaft, while the internal pull wire extends internally through the proximal portion of the shaft adjacent to the external pull wire, and extends internally through the distal portion of the shaft.

23 Claims, 9 Drawing Sheets

(51) Int. Cl.
  *A61F 2/24* (2006.01)
  *A61M 25/09* (2006.01)
  *A61M 60/135* (2021.01)
  *A61M 60/148* (2021.01)
  *A61M 25/10* (2013.01)
  *A61B 17/00* (2006.01)

(52) U.S. Cl.
  CPC .......... *A61M 25/09* (2013.01); *A61M 60/135* (2021.01); *A61M 60/148* (2021.01); *A61B 2017/00243* (2013.01); *A61B 2017/00327* (2013.01); *A61M 25/10* (2013.01); *A61M 2210/125* (2013.01)

(58) Field of Classification Search
  CPC ............ A61M 1/125; A61M 2210/125; A61M 60/857; A61M 60/148; A61M 60/135; A61B 17/3468; A61B 2017/00243; A61B 2017/003; A61B 2017/00318; A61B 2017/00323; A61B 2017/00327; A61B 2017/2908; A61F 2/2427–2439
  See application file for complete search history.

(56) References Cited

U.S. PATENT DOCUMENTS

| | | | |
|---|---|---|---|
| 5,873,842 A | 2/1999 | Brennen et al. | |
| 6,004,280 A | 12/1999 | Buck et al. | |
| 6,183,463 B1* | 2/2001 | Webster, Jr. | ........ A61B 18/1492 604/528 |
| 6,592,581 B2 | 7/2003 | Bowe | |
| 6,613,046 B1 | 9/2003 | Jenkins et al. | |
| 7,056,314 B1 | 6/2006 | Florio et al. | |
| 7,115,134 B2 | 10/2006 | Chambers | |
| 7,481,805 B2 | 1/2009 | Magnusson | |
| 7,647,124 B2 | 1/2010 | Williams | |
| 7,729,782 B2 | 6/2010 | Williams et al. | |
| 8,096,985 B2 | 1/2012 | Legaspi et al. | |
| 8,235,916 B2 | 8/2012 | Whiting et al. | |
| 8,435,227 B2 | 5/2013 | Takagi et al. | |
| 8,606,369 B2 | 12/2013 | Williams et al. | |
| 8,827,982 B2 | 9/2014 | Goode et al. | |
| 8,926,588 B2 | 1/2015 | Berthiaume et al. | |
| 8,996,135 B2 | 3/2015 | Elencwajg | |
| 9,072,872 B2 | 7/2015 | Asleson et al. | |
| 9,078,994 B2 | 7/2015 | Rosenman et al. | |
| 9,173,646 B2 | 11/2015 | Fabro | |
| 9,220,874 B2 | 12/2015 | Pillai et al. | |
| 9,320,564 B2 | 4/2016 | Avitall et al. | |
| 9,511,205 B2 | 12/2016 | Inoue | |
| 9,616,197 B2 | 4/2017 | Serina et al. | |
| 9,814,814 B2 | 11/2017 | Corbett et al. | |
| 10,105,221 B2 | 10/2018 | Siegel | |
| 2001/0005789 A1 | 6/2001 | Root et al. | |
| 2003/0114832 A1* | 6/2003 | Kohler | .............. A61M 25/0136 604/528 |
| 2004/0003819 A1 | 1/2004 | St. Goar et al. | |
| 2004/0127847 A1 | 7/2004 | DuBois | |
| 2006/0089618 A1* | 4/2006 | McFerran | ......... A61M 25/0053 604/525 |
| 2006/0155158 A1 | 7/2006 | Aboul-Hosn | |
| 2006/0167535 A1 | 7/2006 | Johnson | |
| 2006/0217794 A1 | 9/2006 | Ruiz et al. | |
| 2007/0032850 A1 | 2/2007 | Ruiz et al. | |
| 2007/0049906 A1 | 3/2007 | Magnusson | |
| 2007/0060914 A1 | 3/2007 | Magnusson | |
| 2007/0100299 A1 | 5/2007 | Magnusson | |
| 2007/0112422 A1 | 5/2007 | Dehdashtian | |
| 2007/0156233 A1 | 7/2007 | Kapadia et al. | |
| 2007/0299403 A1 | 12/2007 | Crowe et al. | |
| 2010/0114306 A1* | 5/2010 | Lenihan | .............. A61B 17/0401 623/2.11 |
| 2010/0160725 A1 | 6/2010 | Kiser et al. | |
| 2010/0185172 A1 | 7/2010 | Fabro | |
| 2010/0198056 A1 | 8/2010 | Fabro et al. | |
| 2010/0198192 A1 | 8/2010 | Serina et al. | |
| 2010/0198208 A1 | 8/2010 | Napp et al. | |
| 2010/0249491 A1 | 9/2010 | Farnan et al. | |
| 2011/0022057 A1 | 1/2011 | Eigler et al. | |
| 2012/0041422 A1 | 2/2012 | Whiting et al. | |
| 2012/0101442 A1 | 4/2012 | Legaspi et al. | |
| 2012/0172656 A1 | 7/2012 | Walters et al. | |
| 2014/0107399 A1 | 4/2014 | Spence | |
| 2014/0276395 A1 | 9/2014 | Wilson et al. | |
| 2014/0276782 A1 | 9/2014 | Paskar | |
| 2014/0276904 A1 | 9/2014 | Hanson et al. | |
| 2014/0303719 A1 | 10/2014 | Cox et al. | |
| 2014/0371719 A1 | 12/2014 | Carnevale | |
| 2015/0258312 A1 | 9/2015 | Tuseth | |
| 2015/0273136 A1 | 10/2015 | Osiev | |
| 2015/0305864 A1 | 10/2015 | Quadri et al. | |
| 2015/0328382 A1 | 11/2015 | Corbett et al. | |
| 2016/0022961 A1* | 1/2016 | Rosenman | ........ A61M 25/0138 604/95.04 |
| 2016/0066993 A1 | 3/2016 | Avitall et al. | |
| 2016/0074623 A1 | 3/2016 | Pillai et al. | |
| 2016/0158506 A1 | 6/2016 | Eliasen et al. | |
| 2016/0213472 A1 | 7/2016 | Kim | |
| 2016/0220785 A1 | 8/2016 | Fabro | |
| 2016/0317288 A1 | 11/2016 | Rogers et al. | |
| 2016/0317289 A1 | 11/2016 | Tozzi | |
| 2016/0367787 A1* | 12/2016 | Van Hoven | ............. A61F 2/246 |
| 2017/0106170 A1* | 4/2017 | Hsueh | ............... A61M 25/0147 |
| 2017/0224483 A1 | 8/2017 | Kizuka | |
| 2017/0245988 A1 | 8/2017 | Siegel et al. | |
| 2017/0258614 A1 | 9/2017 | Griffin | |
| 2017/0361065 A1 | 12/2017 | Legaspi et al. | |
| 2018/0043132 A1 | 2/2018 | Serina et al. | |
| 2018/0078370 A1 | 3/2018 | Kovalsky et al. | |
| 2018/0104398 A1 | 4/2018 | Corbett et al. | |
| 2018/0311421 A1 | 11/2018 | Tuseth et al. | |
| 2018/0318079 A1 | 11/2018 | Patel et al. | |
| 2019/0117937 A1 | 4/2019 | Humphrey et al. | |
| 2019/0151614 A1 | 5/2019 | Hsueh et al. | |

FOREIGN PATENT DOCUMENTS

| | | |
|---|---|---|
| EP | 2687254 B1 | 4/2015 |
| EP | 2913080 A2 | 9/2015 |
| EP | 3142721 A1 | 3/2017 |
| EP | 3288491 A1 | 3/2018 |
| EP | 3302363 A1 | 4/2018 |
| WO | 200060995 A2 | 10/2000 |
| WO | 2005037345 A2 | 4/2005 |
| WO | 2006052651 A1 | 5/2006 |
| WO | 2007149974 A2 | 12/2007 |
| WO | 2008012914 A1 | 1/2008 |
| WO | 2009137712 A1 | 11/2009 |
| WO | 2010085456 A1 | 7/2010 |
| WO | 2010085457 A1 | 7/2010 |
| WO | 2012178115 A2 | 12/2012 |
| WO | 2013181397 A1 | 12/2013 |
| WO | 2014065714 A2 | 5/2014 |
| WO | 2014138482 A1 | 9/2014 |
| WO | 2014197962 A1 | 12/2014 |
| WO | 2015175718 A1 | 11/2015 |
| WO | 2016176409 A1 | 11/2016 |
| WO | 2016196933 A1 | 12/2016 |
| WO | 2017139246 A1 | 8/2017 |
| WO | 2017155892 A1 | 9/2017 |
| WO | 1994003227 A1 | 4/2018 |
| WO | 2018098210 A2 | 5/2018 |
| WO | 2019055154 A2 | 3/2019 |

OTHER PUBLICATIONS

International Search Report and Written Opinion for PCT/US2017/062913 dated Feb. 8, 2018.

(56) References Cited

OTHER PUBLICATIONS

International Search Report and Written Opinion for corresponding PCT/US2020/017370 dated Nov. 6, 2020.

* cited by examiner

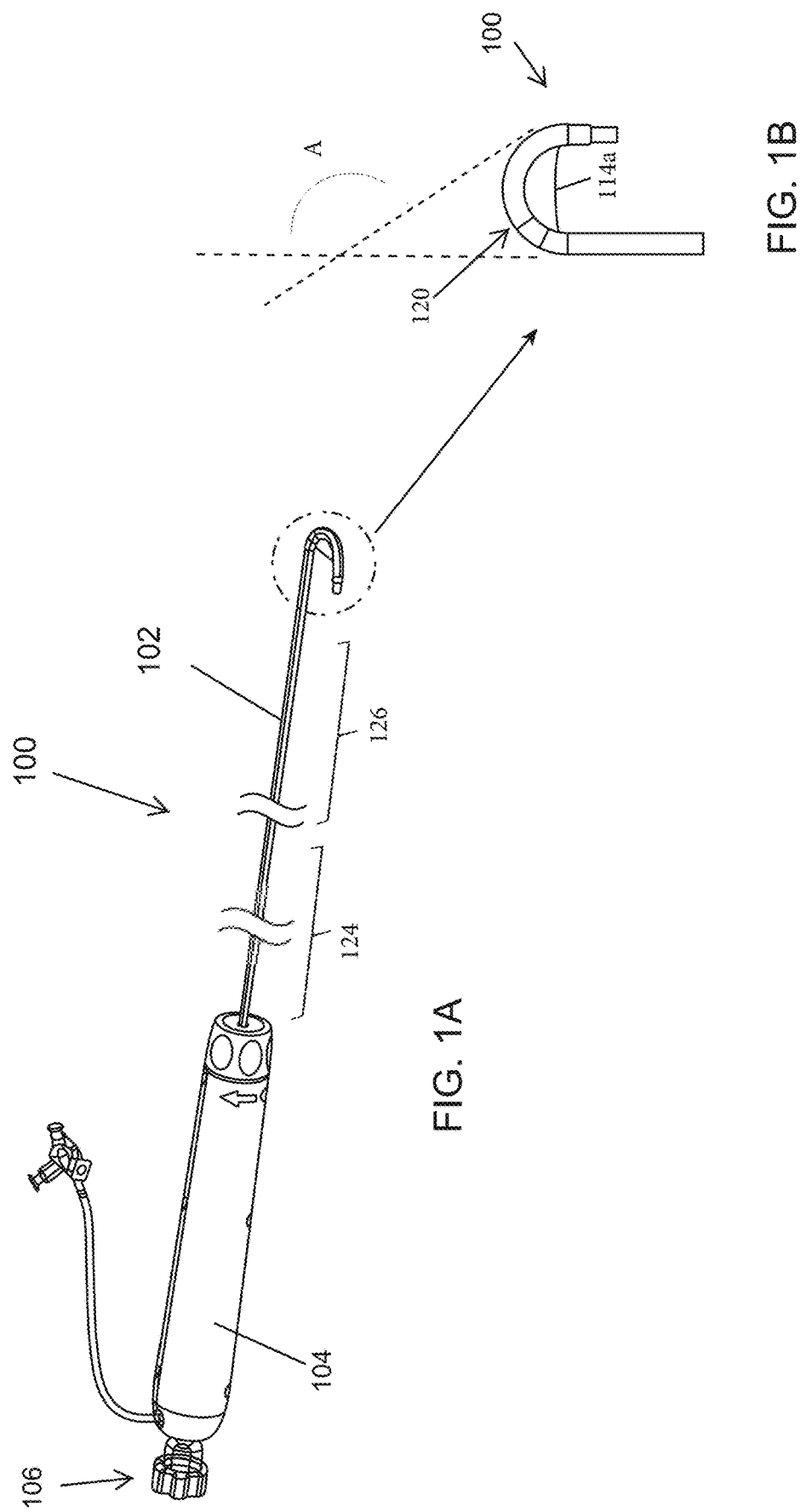

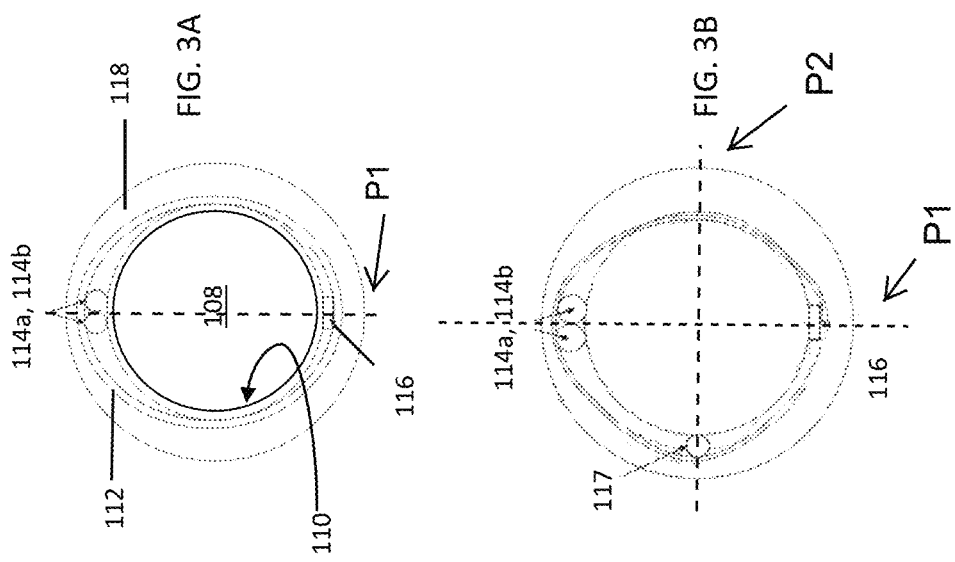
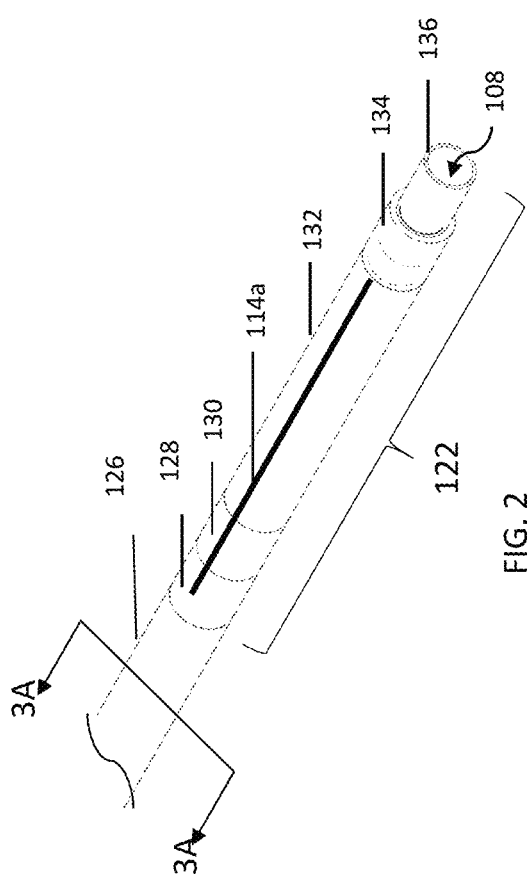

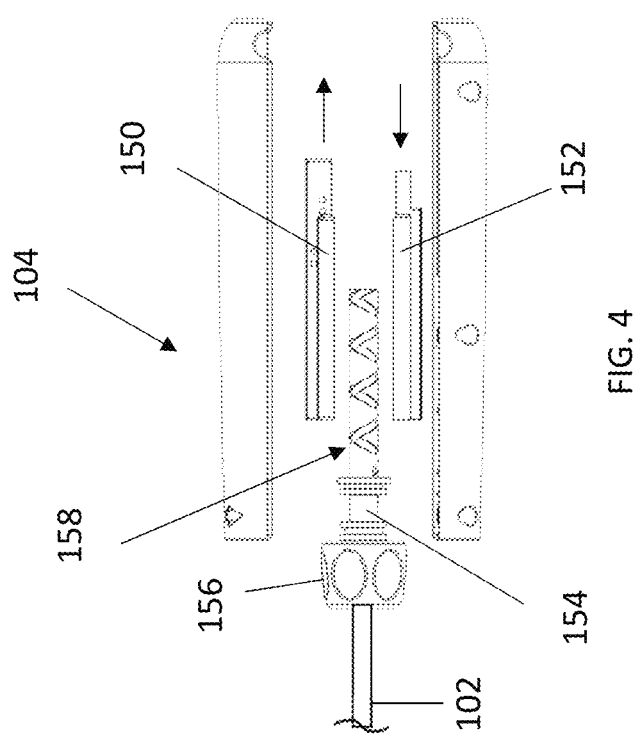

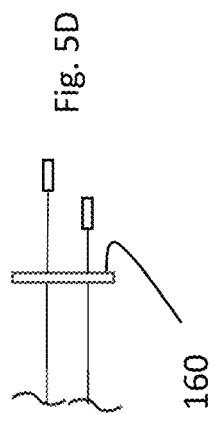
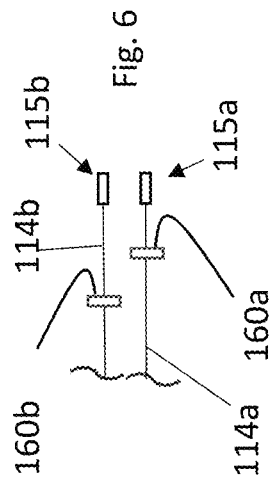
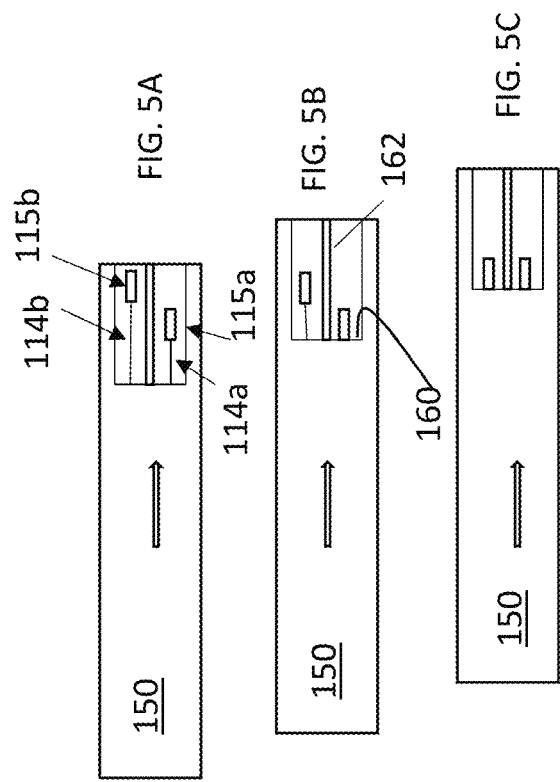

INSTRUMENT FOR FACILITATING TRANSSEPTAL DELIVERY OF CARDIAC THERAPEUTIC DEVICES

This application claims the benefit of U.S. Provisional Application No. 62/802,212, filed Feb. 7, 2019, which is incorporated hereby reference.

BACKGROUND

Various medical procedures in use today involve passage of devices from the right side of the heart to the left side across the inter-atrial septum in a well-established technique known as transseptal catheterization.

Commonly owned application Ser. No. 16/578,375, entitled Systems and Methods for Transseptal Delivery of Percutaneous Ventricular Assist Devices and Other Non-Guidewire Based Transvascular Therapeutic Devices, filed Sep. 22, 2019, which is incorporated herein by reference, discloses a system and method for delivering therapeutic devices positionable at the aortic valve, and gives as a primary example pVADs. In that application, transseptal catheterization is used to deliver a long flexible cable such that it extends from the venous vasculature through the heart to the arterial vasculature. Once positioned the cable has one end extending from the right subclavian vein and an opposite end extending from the right or left femoral artery. A grasper is attached to the cable at the femoral artery, and the cable is withdrawn from the right subclavian vein to position the grasper along the route previously occupied by the cable. The grasper is then attached at the right subclavian vein to a pVAD and pulled from the femoral artery while the pVAD is simultaneously pushed at the right subclavian vein. This combination of pulling and pushing force moves the pVAD into the heart, across the septum and the mitral valves, and into its final position at the aortic valve.

Commonly owned co-pending application PCT/US2017/62913, filed Nov. 22, 2017 and Published as WO/2018/098210, which is incorporated herein by reference, discloses a system and method for delivering mitral valve therapeutic devices to the heart (such as devices for positioning a replacement mitral valve or devices for treating a native mitral valve) using a transseptal approach. In that application, transseptal catheterization is used to position a cable that helps to deliver a therapeutic device to the mitral valve site. Once it is positioned the cable has one end extending from the right femoral vein and an opposite end extending from the left or right femoral artery. The mitral valve therapeutic device is attached to the cable at the right femoral vein. The cable is then pulled at the femoral artery while the mitral valve therapeutic device is simultaneously pushed at the right femoral vein. This combination of pulling and pushing force moves the mitral valve therapeutic device into the heart, across the septum and to its final position at the mitral valve.

A common challenge of each of the above procedures is the need to prevent the cable or grasper from causing major leakage or damage to the mitral valve leaflets and the mitral valve chordae tendineae, especially when strong forces are being used to push and pull the potentially bulky therapeutic device (e.g. the pVAD or mitral valve therapeutic device) across the interatrial septum and downwardly into the mitral valve, there is a strong tendency to cause the loop of the cable running through the heart to be pulled upwardly into the valve structures. This application describes a left ventricle redirector "LVR" configured to retain the cable lower in the heart during this step, where it can safely avoid the mitral valve structures. The LVR also includes steering capability that can be used to aid in the steering of the therapeutic device through the mitral valve. This can help with final steering of a mitral valve therapeutic device into the center of the mitral valve ring at an angle that is perpendicular to the mitral valve ring plane. For procedures where the therapeutic device is to be positioned at or across the aortic valve (such as a pVAD or aortic valve therapeutic device) the steering allows movement of the pVAD safely through the center of the mitral valve with optimal final positioning across the aortic valve.

Another protective function served by the disclosed LVR is the isolation of the shaft of the cable or grasper from surrounding tissue at times when the cable/grasper is under load. In each of the above procedures, the step of pushing or pulling the cable or grasper is carried out with that device extending through the LVR, so that the walls of the LVR shaft prevent direct contact between the grasper/cable and the surrounding tissue and passages. This avoids disruption of the valve structures or damage to the cardiac apex when a pushing force or tension is applied to the grasper or cable.

BRIEF DESCRIPTION OF THE DRAWINGS

FIG. 1 is a perspective view of a left ventricle redirector ("LVR").

FIG. 1B is a side elevation view of the distal tip section of the LVR in the curved position.

FIG. 2 is a perspective view of the distal tip section of FIG. 1B in the straight position.

FIG. 3A is a cross-section view of the LVR of FIG. 1, taken along the plane designated 3A-3A in FIG. 2.

FIG. 3B is similar to FIG. 3A but it shows an alternative construction of the LVR shaft.

FIG. 4 is an exploded view of the handle of FIG. 1.

FIGS. 5A-5C are a sequence of drawings schematically illustrating movement of the pull wire slider during activation and locking of the pull wires.

FIG. 5D is similar to FIG. 5C but shows only the pull wires and the engagement feature of the slider.

FIG. 6 is similar to FIG. 5D but shows an alternative configuration of pull wires and engagement features for the slider.

DETAILED DESCRIPTION

Figure 1D:
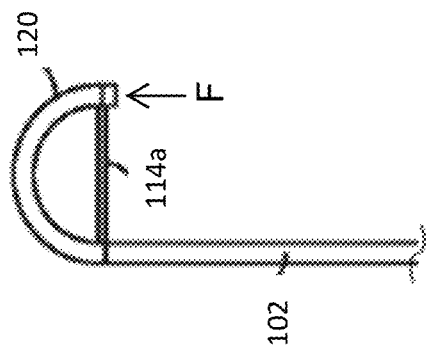
FIGS. 1C and 1D are side elevation views of alternative embodiments of distal tip sections for the LVR, each shown in the curved position.
Figure 1C:
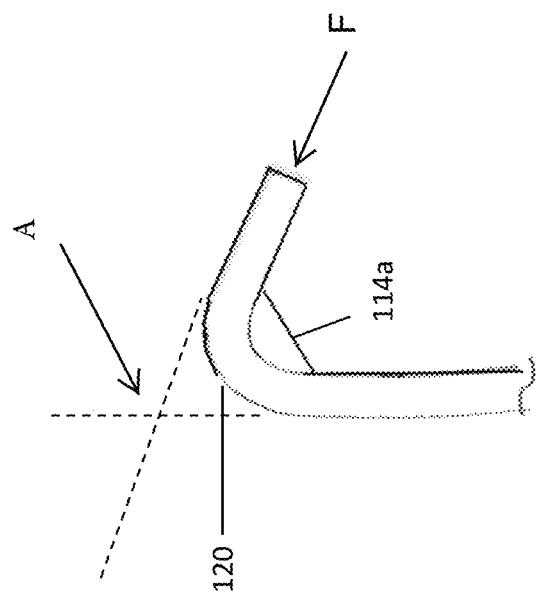

An embodiment of a left ventricle redirector (LVR) is shown in FIGS. 1A-3A. It includes an elongate catheter shaft 102 having a proximal handle 104 with a proximal access port 106 and a flush port. The shaft includes a lumen accessible via the port access port 102. This lumen extends to the distal tip of the shaft.

FIG. 3A is a cross-section view showing the shaft construction. As shown, a lubricious layer such as an extruded PTFE liner 110 lines the wall of the lumen 108, and a braid 112 covers the liner 110. Incorporated between the liner 110 and braid 112 are a pair of pull wires 114a, 114 and a return wire 116. The pull wires 114a, 114b are directly adjacent to one another. Their side-by-side positioning causes bending of the LVR along a bending plane P1 when tension on the wires is increased. The return wire 116 is positioned 180° from the pull wires as shown. It may have a rectangular diameter with the long edges oriented to cause the shaft to preferentially bend along bending plane P1. One of the pull wires 114a exits and then re-enters the shaft towards the shaft's distal end. This will be explained in the description of FIGS. 1B and 2.

An outer jacket 118 of polymeric material (e.g. polyether block amide, "PEBA," such as that sold under the brand name Pebax) covers the braid 112. During manufacture of the shaft, the polymeric material is positioned over the braid and subjected to a reflow process to flow the polymeric material over the braid. The material properties of the polymeric material vary along the length of the shaft. This is discussed below.

The distal end of the shaft is moveable between the generally straight position shown in FIG. 2, and an articulated position in which the distal end is formed into a curve, as shown in FIG. 1B. The parts of the shaft that are proximal to the curve 120 may be collectively referred to as the main body of the shaft. The maximum articulation angle A is in the range of 100-140 degrees, with a more preferred range of 110-135 degrees, but may be different depending on the application for which the LVR will be used. The handle 104 (FIG. 1A) includes actuators to actuate the pull wires 114a, 114b to bend the shaft and to actuate the return wire 116 to return the distal end of the shaft to the generally straight configuration.

One of the pull wires 114a exits the sidewall of the shaft near the shaft's distal end, runs along the exterior of the shaft in a distal direction, and re-enters the shaft at the distal end of the shaft, while the other pull wire 114b does not exit the shaft at the distal end. The dual pull wire configuration advantageously allows articulation to the desired curvature and locking of the articulation in that curvature despite high loads experienced at the tip of the LVR during use.

The pull wire 114b that remains inside the shaft ("internal pull wire") helps maintain the patency of the shaft's lumen during articulation, preventing the shaft from buckling or kinking despite the large degree of articulation as would likely happen if the construction used only the external pull wire.

The pull wire 114a that exits the shaft (the "external pull wire") functions as a locking mechanism to lock the shaft in its articulated orientation, preventing the curve from opening when the outer circumference of the curve is against the left ventricular apex and forces are exerted against the distal tip of the LVR. During use of the LVR in the manner described in the discussion of FIGS. 7 and 8 and in the above-referenced co-pending patent applications, such forces will include forces along vectors that, without the locking provided by the external pull wire 114a, would push the distal end out of its articulated shape and towards a more straight position. The locking achieved by the pull wire 114a causes the LVR to generally retain its original shape of articulation when subjected to over approximately 40N, over approximately 50N or 60N, and even over approximately 70N along those vectors (including in an axial direction against the tip as depicted by arrow F in FIGS. 1C and 1D). The loading capability is dependent on the wire size and construction and can be tailored to suit the application for which the LVR is needed. By "generally retain its original shape of articulation" it is meant that the shape of the curve in the region bridged by the external pull wire 114a (region 132) does not significantly change. In one experiment, an LVR of wall thickness 0.026" retained its articulated shape when subjected to an axial force F of 72.5 N on the distal tip of the articulated LVR, whereas an identical LVR made of the same wall thickness but without the pull wire 114a lost its articulated shape under a force F of less than 20N.

Another, related, feature of the LVR is that when its tip is subjected to the forces described in the prior paragraph, the length of the pull wire 114b that is exposed outside the shaft 102 remains generally constant.

Note that the terms "pull wire" and "wire" are not intended to mean that the pull wires must be formed of wire, as these terms are used more broadly in this application to represent any sort of tendon, cable, or other elongate element the tension on which may be adjusted to change the shape of the LVR. Also, while the term "straight" is used to refer to the shape of the LVR distal portion in its non-articulated position, it should be pointed out that the catheter's inherent flexibility in the non-articulated position may cause it to bend under forces of gravity when held upright, or to curve when tracked over a curved cable or wire, or advanced into contact with another structure. The term "straight" thus should not be used to interpret this application or the corresponding claims as requiring the distal portion of the shaft to hold a straight shape when in the non-articulated position.

The pull wire and return wire configuration shown in FIG. 3A also provides for steering in two directions, with movement occurring along one plane P1 between straight and curved positions. Other embodiments can be configured with additional directions of movement if desired.

The shape of the curve formed on actuation of the pull wires may differ for different embodiments. In the example shown in FIGS. 1B and 1D, the shaft curves about a relatively large radius as shown to produce a fairly shallow curve. In these embodiments, the straight portion of the distal end that extends beyond the curve 120 has a longitudinal axis that is parallel to the longitudinal axis of the main body of the shaft. In another embodiment shown in FIG. 1C, the shaft curves about a relatively small radius. In this embodiment, the straight portion that extends beyond the curve has a longitudinal axis that is transverse to the longitudinal axis of the main body. In a preferred embodiment, the diameter of the curve (i.e. the length along a line extending from the inside of the curve at the distal tip to where it perpendicularly intersects the main body of the shaft) is preferably in the range of 2.5-3.5 cm.

The distance between the distal location at which the pull wire 114a re-enters the shaft and the distalmost end of the shaft tip may also vary between embodiments. In the FIGS. 1B and 1C embodiments, that entry site may be spaced 10 or more mm from the distalmost end of the shaft tip, whereas in the FIG. 1D embodiment, the entry site may be spaced 5 mm or less from it.

The cross-section view of FIG. 3B shows a modified construction in which the shaft includes an additional reinforcing wire 117. Reinforcing wire 117 is positioned orthogonal to the radius extending between the side-by-side pull wires 114a, 114b to the longitudinal axis of the shaft. This shaft is particularly useful in applications where the LVR is subjected to particularly high loads during use, such as when it is being used to aid delivery of a mitral valve therapeutic device (such as a mitral valve delivery device carrying a mitral valve) to the mitral valve site, as described in co-pending application WO/2018/098210.

Material properties of the LVR components will next be described, although materials having different properties may be used without departing from the scope of the invention. The materials for the shaft are selected to give the LVR enough column strength to be pushed through the vasculature, torqued, and tracked over a cable or wire through the aortic arch, articulated at the distal tip section 122 without kinking, and to allow the outer circumference of the curve formed when it is articulated to be pressed into the left ventricle away from the mitral and aortic valves as will be described in connection with FIGS. 7 and 8. As discussed in the description of FIG. 3A, a wire braid 112 extends through the shaft 102 to enhance the torque-ability of the LVR. A lubricious liner 110 made using PTFE, ultra-high molecular weight polyethylene (UHMWPE) or like material also extends through the shaft, allowing smooth relative movement between the LVR and the wires or cables that pass through it during use. The braid and liner terminate in the distal tip section 122 as will be described with respect to FIG. 3A.

Referring to FIG. 1A, the shaft 102 is of sufficient length to extend from the right or left femoral artery, up the descending aorta around the aortic arch and through the aortic valve into the left ventricle ("LV"), so that the distal tip section 122 can be moved into its curved position and seated at the LV apex. To meet this requirement, the length of shaft extending from the handle may have a length in the range of 900-1200 mm, and more preferably in the range of 1000-1100 mm. The materials used for the outer jacket 118 of the shaft vary along the shaft's length. The shaft includes a rigid section, formed of L25 nylon or similar material, that is disposed within the handle. In the most proximal section 124 of the shaft lying outside the handle, the jacket is formed of fairly rigid polymer material of at least 72D shore hardness to give the LVR the column strength needed for advancement through the vasculature. When the LVR is positioned with the curve in the left ventricle, this section sits within the aortic arch and externalizes through the introducer in the femoral artery. Within the handle, the jacket 118 may include both 72D PEBA and L25 Nylon, to further enhance column strength.

The next most distal section 126 uses a somewhat more flexible, but not highly flexible, material, such as 55D PEBA or similar material. Segment 126, during use, traverses the aortic arch and sits within the left ventricle.

Referring now to FIG. 2 which shows the distal tip section in its straight position. The distal tip section 122 of the preferred embodiment includes five segments. In each of these segments the outer jacket 118 has different rigidity compared with the adjacent segments. The most proximal of these segments 128 is adjacent to section 126 described in the previous paragraph. It is a short section with a jacket of a rigid material (e.g. 72D PEBA). It is through the wall of this segment that the pull wire 114a extends from inside the shaft to outside the shaft. The rigid material helps prevent tearing around the opening through which the pull wire passes 114a even when the pull wire is highly tensioned.

In the distally adjacent segment 130, a slightly less rigid material is used (e.g. 55D PEBA). This is done to provide a gradual transition between the rigid segment 128 and the next adjacent segment 132 which is highly flexible. The transition segment helps to avoid buckling.

Segment 132 is the longest segment within the distal tip section 122 and it is designed to facilitate bending of the shaft into the curve during articulation using the pull wires. It has a jacket made from a very flexible material (e.g. 35D PEBA). The braid 112 (not shown in FIG. 2) terminates at the distal end of this segment 132. The external pull wire 114a extends along the exterior surface of section 122 as shown in FIG. 2.

Distally adjacent to flexible segment 132 is the segment 134 in which the pull wire 114a re-enters the shaft, and it is also the segment in which the pull wires 114a, 114b and return wire 116 are anchored to a pull ring (visible in dashed lines in FIG. 2). It is formed of a rigid material (e.g. 72D PEBA). The lubricious liner 110 may terminate at the distal end of segment 134.

The distalmost segment 136 provides an atraumatic tip for the shaft. Also, during use of the LVR during medical procedures, another device is inserted into, pressed axially against, or received by, its distal tip as it is held securely in the left ventricle or disposed in the vasculature. The segment 136 must have sufficient wall thickness so that it will not collapse or tear when the other device (e.g. the RLC, discussed below in connection with FIG. 7 and described in co-pending application Ser. No. 16/578,375, the segmental tensioner described in co-pending application WO/2018/098210, or the advancer that is engaged by the grasper as described in co-pending application Ser. No. 16/578,375 is inserted into it. It is formed of highly flexible polymeric material, such as 35D PEBA, having a sufficiently thick wall thickness and luminal diameter to be able to receive the device without collapsing.

In one embodiment, the polymeric material of the distal segment 134 is doped with BaSO4 to allow the tip of the LVR to be seen on the fluoroscopic image. Alternatively, a marker band made from radiopaque material may be positioned near the tip.

The flexural properties, and thus the stiffness, of the LVR are sensitive to the durometer of the extrusions forming the shaft, the reinforcement configurations used in the shaft (e.g. the braid and reinforcing wire 117) and the geometry of the shaft. Table A below illustrates the gradient of polymer stiffness from region 132 of the shaft to region 126 for three different embodiments, the first being the first embodiment described above and having the cross-section shown in FIG. 3A, an inner diameter of approximately 10.3 Fr and an outer diameter of 14.5-15.3 Fr. The second embodiment is a slightly modified embodiment which has the cross-section shown in FIG. 3B, an inner diameter of 8.3 Fr and an outer diameter of 12-13 Fr. The third embodiment is a lower profile device having an inner diameter of 6 Fr and an outer diameter of 9 Fr.

TABLE A

| Embodiment | Region 132 | Region 126 | Region 124 | | Polymer Gradient from Region 132 to 126 |
|---|---|---|---|---|---|
| 1 | 35D  21 MPa | 55D  170 MPa | 72D-L25 | 510-1500 MPa | 8 |
| 2 | 35D  21 MPa | 55D  170 MPa | 72D | 510 MPa | 8 |
| 3 | 80A  ~4 MPa | 72D  510 MPa | L25 | 1500 MPa | 128 |

Figure 9A:
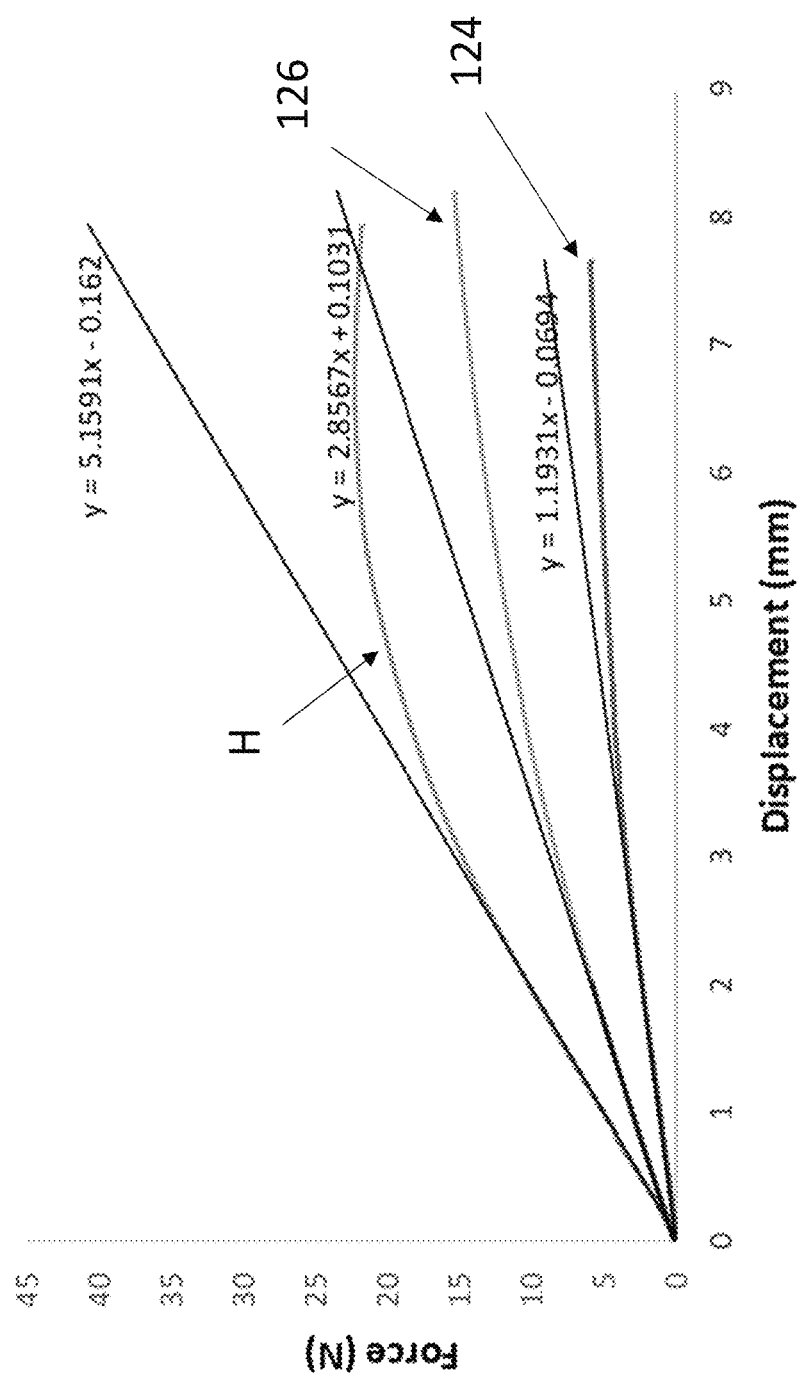
FIG. 9A is a graph showing force versus displacement for sections of the shaft of the LVR described herein.

Embodiment 1 is provided with larger cross-sectional dimensions (wall thickness and diameter) than the other embodiments and can thus provide stiffness equivalent to that of Embodiment 2, without the need for the reinforcing wire 117. The region rigidity of the shaft increases by a factor of approximately two as it transitions from region 126 proximally to the region that is disposed within the handle. FIG. 9A depicts the flexural performance of regions 126, 124 and the region H of the shaft that is disposed in the handle in a shaft made with materials listed on Table A.

Embodiment 2 depicted on the table above, includes the reinforcing wire 117 described in connection with FIG. 3B. This construction provides the shaft with two perpendicular planes of stiffness. The first, flexible, plane of stiffness P1 coincides with the plane of articulation of the LVR. It accommodates tracking of the LVR from the descending aorta and over the aortic arch. The second, stiffer plane of stiffness P2 is created by the reinforcing wire 117. It provides both column strength and positional stability of the LVR within the ventricle. This enhances the positional integrity of the LVR as it is steered to center the mitral valve therapeutic device within the mitral valve site. In some embodiments, the shaft is 50-70%, and more preferably 55%-65% stiffer along bending plane P2 than along bending plane P1. This shaft is particularly useful in applications where the LVR is subjected to particularly high loads during use, such as when it is being used to aid delivery of a bulky and stiff mitral valve therapeutic device (such as a mitral valve delivery device carrying a mitral valve) to the mitral valve site, as described in co-pending application WO/2018/098210.

Figure 9B:
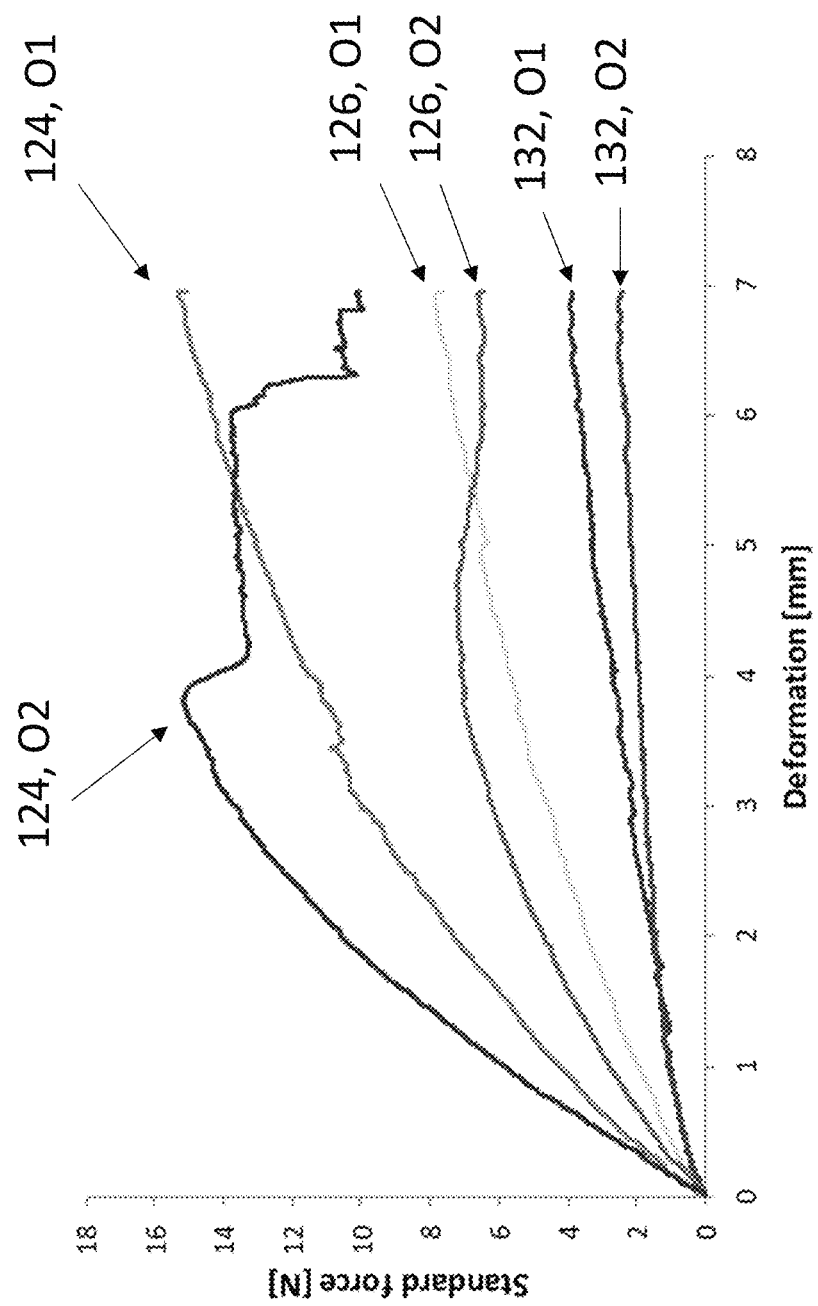
FIG. 9B is a graph showing force versus displacement for sections of the shaft of a second embodiment of an LVR shaft described herein along two orthogonal stiffness planes.

FIG. 9B shows, flexural performance data for each of the regions 132, 126, 124 of Embodiment 2 when constructed with the material properties represented on Table A. Performance data is shown both for stiffness plane P1 and stiffness plane P2. This illustrates that the stiffness of each region of the shaft increases by a factor of 2 from distal to proximal on stiffness plane P1. On stiffness plane P2, the presence of the reinforcing wire increases rigidity by approximately 60% relative to stiffness plane P1.

Embodiment 3 is provided with smaller cross-sectional dimensions, but it uses higher durometer polymers without a reinforcing wire 117. Compared with the other embodiments, it uses a lower durometer polymer in the articulation region 132 to ensure that the stiffness gradient through the length of the shaft localizes articulation to the region of the external pull wire 114a. This embodiment has a lower overall stiffness than the other two embodiments.

Figure 9C:
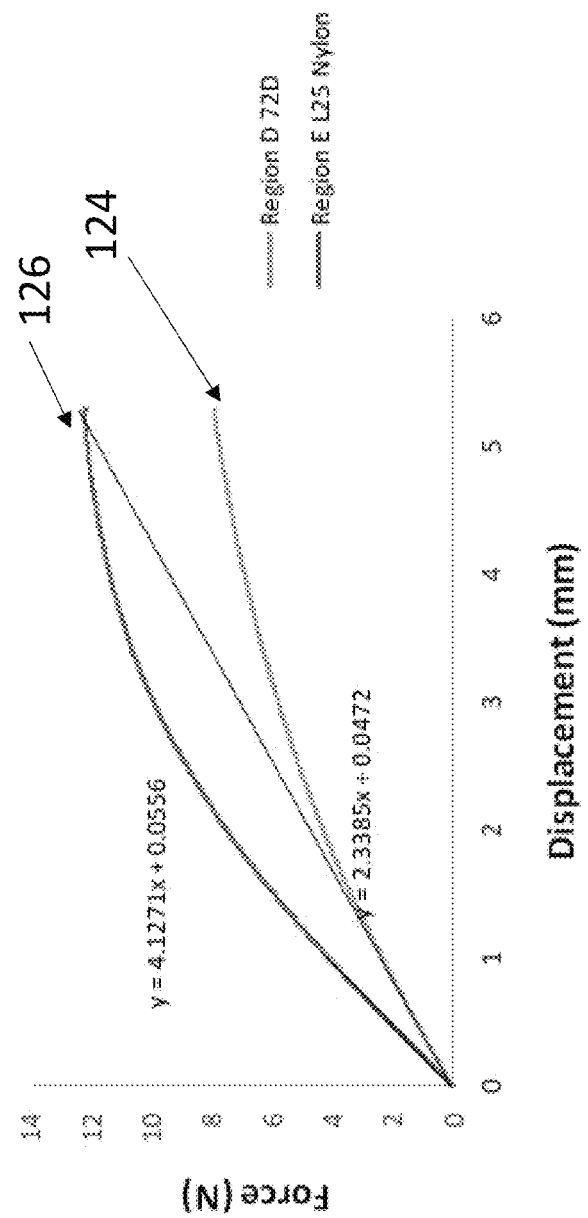
FIG. 9C is a graph showing force versus displacement for sections of the shaft of a third embodiment of an LVR shaft described herein.

FIG. 9C depicts the flexural performance of Regions 126, 124 of the shaft of Embodiment 3 when it is constructed to have the material properties represented on Table A. As illustrated, stiffness increases by a factor of two from region 126 to the more proximal region 124.

A discussion of the actuation mechanism for the pull wires 114a, 114b and return wire 116 will next be described.

In general, the handle 104 is configured to move the pull wires 114a, 114b in a first direction (preferably proximally) while simultaneously moving the return wire 116 in a second, opposite direction (preferably distally), in order to articulate the LVR to the curved position. Reversing the respective directions of motion of the pull wires 114a, 114b and return wire 116 moves the LVR back to the generally straight position.

Referring to FIG. 4, within the handle 104 are a first sliding member 150 and a second sliding member 152, each of which is moveable longitudinally within the handle. For convenience the term "slider" will be used as shorthand for "sliding member."

The handle 104 includes a mechanism for simultaneously moving the sliders 150, 152 in opposite directions. Various mechanisms can be used for this purpose. One exemplary mechanism, shown in FIG. 4, includes a barrel 154 that axially rotates relative to the handle 104 when the user rotates actuation knob 156. Helical features 158 on the barrel 154 are operatively associated with helical features (not visible in the drawings) in each slider 150, 152, with the helical features 158 that interact with slider 150 being of opposite hand to those that interact with slider 152. Thus, rotation of the knob 156 in a first direction causes slider 150 to move proximally while slider 152 moves distally (see arrows in FIG. 4), and rotation of the knob 156 in the opposite direction causes slider 150 to move distally while slider 152 moves proximally. The pull wires 114a, 114b (not shown in FIG. 4) extend into the handle 104 from the LVR shaft 102 and are actuatable by first slider 150, while the return wire 116, which also extends into the handle from the LVR shaft, is actuatable by the second slider 152. With this configuration, motion of the sliders 150, 152 causes both pull wires 114a, 114b to be pulled as the return wire 116 is simultaneously pushed, and vice versa. Note that while the knob 156 and barrel 158 assembly is a convenient way to actuate this motion using a single input from the user, alternative mechanisms can be used without departing from the scope of the claims.

The two pull wires 114a, 114b must travel different distances during articulation, due to the fact that the internal pull wire 114b traverses the curve resulting from the articulation from its position within the shaft, while the external pull wire 114a traverses a shorter path between the point at which it exits the shaft and the point at which it re-enters the shaft. The wires must therefore be actuated at different positions within the handle so as to ensure that the external pull wire 114a maintains equal or greater tension than the internal pull wire 114b. This avoids wire slack and ensures that the locking mechanism does not relax during application of forces F at the LVR's tip.

FIGS. 5A-5C are a sequence of drawings illustrate a configuration for the slider 150 that is designed to actuate the pull wires 114a, 114b from different positions. Each pull wire 114a, 114b is shown with an actuation feature 115a, 115b at its proximal end. The actuation feature can be any feature that will be engaged by a corresponding feature of the slider 150 as the slider moves into contact with the actuation feature. In this embodiment the actuations features 115a, 115b are elements, on the proximal ends of the pull wires, that have diameters wider than the diameter of the pull wire itself. In this particular example, the actuation feature for each wire is its corresponding crimp.

Distal to each actuation feature 115a, 115b is a corresponding feature of the slider that will engage that actuation feature as the slider 150 moves in the proximal direction (indicated by the arrow in FIG. 5A). In the embodiment depicted in the drawings, the pull wires 114a, 114b have their proximal ends positioned proximal to a proximally facing face 160. The pull wires 114a, 114b may extend through openings in the member on which the face is position as illustrated in FIG. 5D. Each opening is smaller in diameter than the diameter of the actuation feature 115a, 115b. The face 160 serves to engage the actuation feature 115a, 115b of each pull wire 114a, 114b as the slider 150 moves proximally. Note that there may be two separate members having faces 160a, 160b (see FIG. 6), one for each of the pull wires 114a, 114b, or the face 160 may be divided by a longitudinal barrier 162 that maintains separation between the proximal ends of each pull wire as shown in FIGS. 5A-5C.

FIG. 5A depicts the slider 150 and pull wires 114a, 114b when the LVR is in the generally straight (non-articulated) position. As shown, the length of the external pull wire 114a is shorter than that of the internal pull wire 114b, so that when the slider 150 moves proximally, the external pull wire 114a is actuated by engagement feature/surface 160 first (FIG. 5B), and it is then pulled a predetermined distance before the internal pull wire 114b is actuated by engagement feature 160 (see FIG. 5C, which shows the pull wires after actuation of the internal pull wire 114b has begun). This ensures that the loading of the external pull wire is higher than, or at least equal to, the external pull wire, as discussed above. From the position shown in FIG. 5C, proximal movement of the slider continues until the pull wires 114a, 114b bring the shaft to its fully articulated position.

In an alternative arrangement shown in FIG. 6, the slider may have separate features 160a, 160b positioned to actuate the pull wires 114a, 114b at different points along the slider's travel. FIG. 6 depicts these features of the slider and the pull wires when the LVR is in the generally straight (non-articulated) position. The features 160a, 160b are positioned on slider so that as slider moves proximally, feature 160a engages external pull wire 114a (e.g. at crimp 115b or other actuation feature as discussed above) and pulls it a predetermined distance before the feature 160b similarly actuates internal pull wire 114b.

In each of the above actuation embodiments, the distance by which external pull wire 114a will travel before internal pull wire 114b is engaged is selected to be the approximate difference between L1 and L2. In this calculation, L1 is the length of external pull wire 114a between its exit and entry points into and out of the shaft when the LVR is in the fully articulated position. L2 is the length traversed by the internal pull wire 114b along the internal circumference of the curve, measured between the points on the internal pull wire's path that are circumferentially adjacent to the points at which the adjacent external pull wire exits and then re-enters the shaft.

Method of Use

Use of the LVR in two different procedures will next be described with reference to FIGS. 7 and 8.

Figure 7:
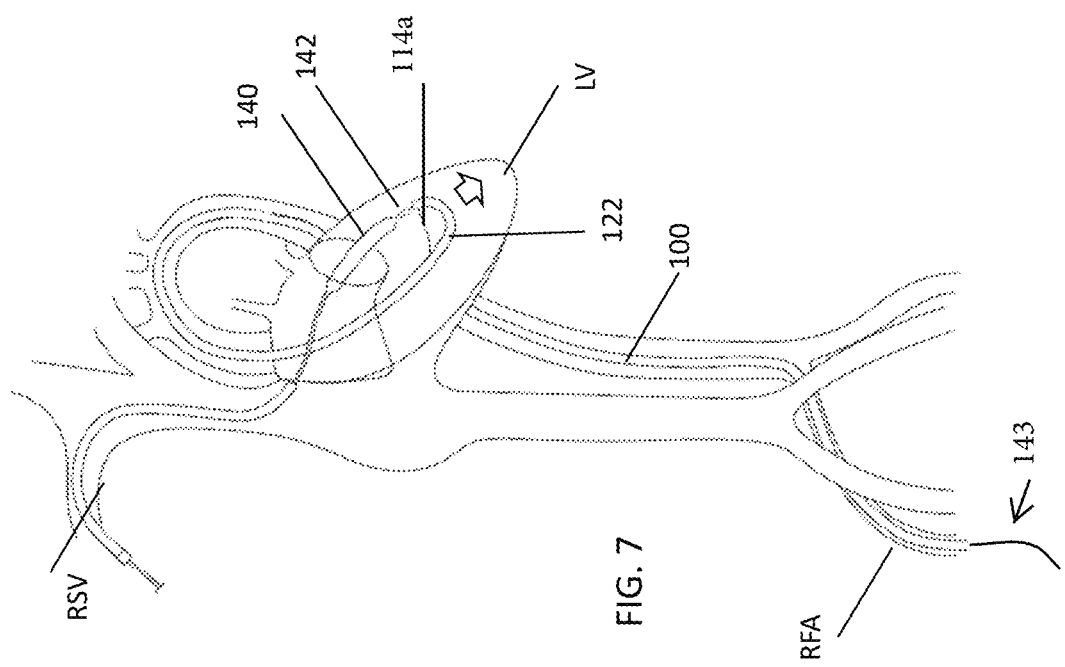
FIG. 7 schematically illustrates use of the LVR in a medical procedure for positioning a therapeutic device such as a pVAD in a patient's heart.

FIG. 7 illustrates use of the LVR in a procedure for positioning a pVAD at an aortic valve of the heart using a superior approach, as described in commonly owned co-pending application Ser. No. 16/578,375. A more detailed description of the full method can be found in that application.

Before making use of the LVAD, transseptal catheterization is used to deliver a long flexible cable such that it extends from the venous vasculature through the heart to the arterial vasculature. Once positioned the cable has one end extending from the right subclavian vein (RSV) and an opposite end extending from the right femoral artery (RFA) or left femoral artery. Additional steps for positioning the cable are described in the co-pending application. After the cable is positioned the LVR may be tracked over the cable to the left ventricle LV. More specifically, the portion of the cable exteriorized at the RFA is backloaded through the LVR on the operating table. The LVR is advanced through the RFA sheath, advanced in the descending aorta and then further advanced around the aortic arch and into its destination in the left ventricle (LV).

The co-pending application describes devices that may be used to ensure that the edges around the open lumen of the LVR do not cause embolization of material from the roof of the aortic arch and to thereby avoid vascular damage or damage to the aortic valve. In one example described in that application a catheter (referred to as the "RLC") extends over the cable from the venous side and extends transseptally with its distal tip positioned in the descending aorta. After the LVR is advanced through the RFA sheath, it is advanced in the descending aorta until it contacts the tip of the RLC, and then both the RLC and the LVR are moved together, with the LVR being advanced as the RLC is being retracted at the same rate so as to keep the ends of the LVR and RLC in contact with one another. After this step the RLC is removed. In another example, the LVR has a dilator positioned at its distal end during its advancement over the cable, eliminating the need to have the RLC against the LVR during advancement of the LVR.

A grasper 143 comprising jaws or another grasping element 142 on a flexible shaft is attached to the part of the cable extending out the proximal end of the LVR at the femoral artery RFA. The other end of the cable is withdrawn from the RSV to draw the grasper along the route previously occupied by the cable, thus positioning the grasper with the grasping end external to the RSV and with the opposite end extending from the RFA. The distal tip section 122 of the LVR, which was previously positioned at the LV, is moved to its curved position by actuating the pull wires using the handle. As discussed above, this action locks the curve in the fully articulated position due to the action of the external pull wire 114a.

At the RSV, the grasping mechanism 142 (e.g. jaws) of the grasper is attached to a flexible pigtail-like member extending from the distal nose of a pVAD 140. The grasper is pulled from the femoral artery RFA while the pVAD is simultaneously pushed at the RSV. This combination of pulling and pushing force moves the pVAD into the heart, across the septum and the mitral valves, and into the LV. As the system advances towards the mitral valve, pushing on the LVR against the left ventricular apex as indicated by the arrow in FIG. 7 helps to keep the grasper and pVAD away from the delicate mitral valve structures. Despite these forces against the distal tip of the LVR, the LVR maintains its curvature because it has been securely locked in the curved position by the external pull wire 114a and the associated actuation features of the LVR's handle.

The grasping mechanism 142 and pig-tail like member of the pVAD enter the distal lumen of the LVR in the LV apex as depicted in FIG. 7. The curved distal end of the LVR may be steered using the handle to change the tension on the pull wires 114a, 114b as the pVAD passes through the mitral valve. This allows movement of the pVAD safely through the center of the mitral valve. Once the grasper and pVAD tip enter the LVR, the curve on the LVR is straightened. The LVR is retracted into the LV outflow tract, the LVR and grasper being pulled together from the RFA as the pVAD is advanced simultaneously from the RSV. The pVAD is moved in this way, with the distal end of the LVR being steered using the pull wires 114a, 114b as needed, until the pVAD reaches its final position at the aortic valve with the inlet resting away from the mitral valve and toward the ventricular apex and the outlet positioned in the ascending aorta.

Figure 8:
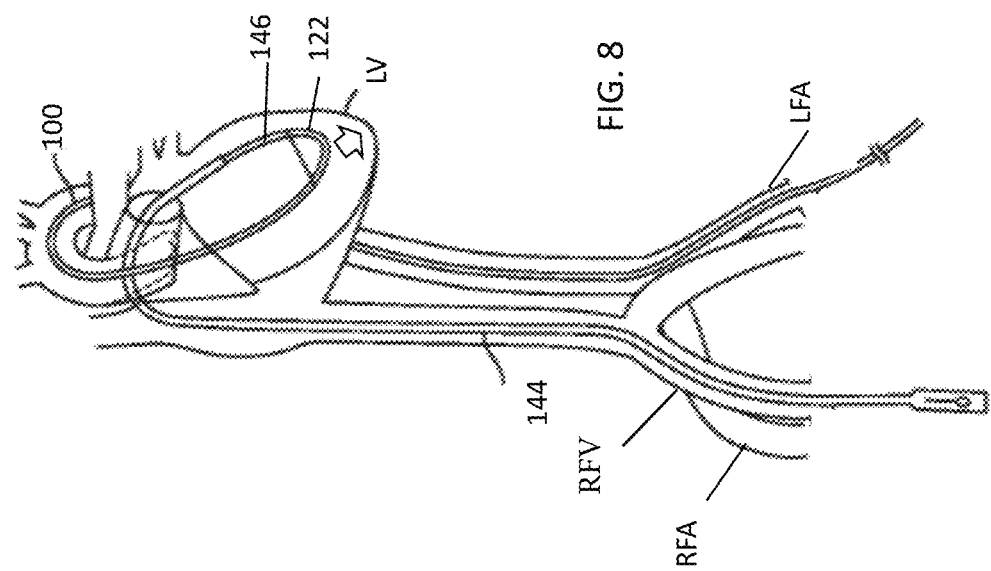
FIG. 8 schematically illustrates use of the LVR in a medical procedure for positioning a therapeutic device such as a mitral valve therapeutic device in a patient's heart.

FIG. 8 illustrates use of the LVR in a procedure for positioning a mitral valve therapeutic device (MVTD) 144, which may be a delivery system for a replacement valve, at a mitral valve of the heart using a femoral approach, as described in commonly owned co-pending application WO/2018/098210. A more detailed description of the full method can be found in that application.

Before making use of the LVR, trans-septal catheterization is used to deliver a long flexible cable such that it extends from the venous vasculature through the heart to the arterial vasculature. Once positioned the cable has one end extending from the left or right femoral vein (RFV) and an opposite end extending from the right femoral artery (RFA) or left femoral artery (LFA—as shown).

A relatively rigid tubular device referred to as a segmental tensioner 146 is positioned over the cable, followed by the MVTD 144, with the distal tip of the MVTD being inserted into a proximal hub on the segmental tensioner. A cable lock locks the MVTD and segmental tensioner 146 assembly onto the cable.

The end of the cable that extends from the femoral artery is backloaded through the LVR on the operating table so that the LVR may be tracked over the cable to the LV. The LVR is advanced through the LFA sheath, advanced in the descending aorta and then further advanced around the aortic arch and into its destination in the left ventricle (LV). As discussed above, measures described in the co-pending application are taken to ensure that the edges around the open lumen of the LVR do not cause embolization of material from the roof of the aortic arch. These measures avoid vascular damage or damage to the aortic valve.

The distal tip section 122 of the LVR is moved to its curved position by actuating the pull wires using the handle, locking the curve in the fully articulated position due to the action of the external pull wire 114a.

The MVTD 144 is pushed from the venous side at the RFV to advance it toward the right atrium, led by the segmental tensioner 146, as the system is pulled by the cable from the LFA at the same rate in a coordinated manner. The segmental tensioner 144 leads the way as it crosses the interatrial septum and provides a gradual transition to the bigger and stiffer MVTD.

At this point, a significant pulling force is applied to the MVTD/tensioner assembly by the cable at the femoral artery. This force is slightly more than the "push" force on the MVTD 144 so as to pull the distal nose of the MVTD down and to the patient's left through the interatrial septum. Despite the pushing force of the LVR into the LV apex, with ever increasing pull force, there is a strong tendency to cause the loop of the cable contained in the steerable section of the LVR to be pulled upward into the mitral valve structures above. This tendency is overcome by the synergistic downward pushing force exerted by the segmental tensioner as it enters the lumen at the distal end of the LVR in the LV apex. It ensures that the cable that runs through the assembly is positioned away from the aortic and mitral valve leaflets and chordae tendineae by maintaining the cable safely away from the valve structures within the LVR's protective sleeve. Despite these forces, the LVR maintains its curved configuration as discussed above.

In addition to the importance of maintaining the cable LV apex, another key function of the LVR is to aid in the final steering of the MVTD into the center of the mitral valve ring at an angle that is perpendicular to the mitral valve ring plane. The user fine tunes the MVTD position within the ring through a combination of adjustments to pull wire tension, torqueing of the LVR, and push-pull of the LVR from the handle.

All patents and patent applications referred to herein, including for purposes of priority, are fully incorporated herein by reference.

We claim:

1. A redirector positionable in a left ventricle, the redirector comprising:
   an elongate shaft having a tubular lumen, the shaft having a proximal portion and a distal portion actively steerable between a generally straight position and a curved position;
   an external pull wire and an internal pull wire, the external and internal pull wires moveable in a proximal direction to move the distal portion along only a single bending plane to the curved position, wherein the external pull wire extends internally through the proximal portion of the shaft and has an exposed portion that extends longitudinally along the exterior of the distal portion of the shaft, wherein the internal pull wire extends internally through the proximal portion of the shaft directly adjacent and in parallel to the external pull wire, and extends internally through the distal portion of the shaft.

2. The redirector of claim 1, wherein the external and internal pull wires are simultaneously actuatable.

3. The redirector of claim 1, further including an actuator operatively associated with the external and internal pull wires, the actuator moveable from a first position in which neither of the external or internal pull wires is actuated, to a second position in which only the external pull wire is actuated, to a third position in which the external and internal pull wires are actuated.

4. The redirector of claim 3, wherein the actuator comprises a handle and a slider moveable relative to the handle along a linear path between the first, second and third positions.

5. The redirector of claim 3, further including a return wire extending through the shaft and a second actuator operatively associated with the return wire, wherein the first and second actuators are operatively coupled such that first and second actuators are moveable simultaneously in opposite directions.

6. The redirector of claim 5, wherein the return wire extends longitudinally through the shaft, parallel to, and positioned 180 degrees from, the internal and external pull wires.

7. The redirector of claim 1, wherein when the shaft is in the curved position, the external pull wire locks the shaft in the curved position.

8. The redirector of claim 7, wherein when the shaft is locked by the external pull wire in the curved position, the shaft retains the shape of the curved position when a distal tip of the shaft is subjected to an axial force of at least one of the following: over 40N, over 50N, over 60N or over 70N.

9. The redirector of claim 7, wherein when the shaft is locked by the external pull wire in the curved position, the external pull wire has an exposed length external to the shaft, and wherein the external pull wire substantially maintains the length of its exposed length when a distal tip of the shaft is subjected to an axial force of at least one of the following: over 40N, over 50N, over 60N, or over 70N.

10. The redirector of claim 1, wherein when the shaft is in the curved position, the internal pull wire extends along an inner circumference of the curve.

11. The redirector of claim 1, wherein the elongate shaft in the curved position has a distal curve with an articulation angle A relative to the longitudinal axis of the proximal portion of the shaft when the proximal portion is positioned in a straight configuration, and wherein the angle A is in the range of 100-140 degrees.

12. The redirector of claim 1, wherein an outer jacket of the shaft includes, proximal to the exposed portion of the external pull wire, at least two regions of differing stiffness, wherein a rigidity of each of the at least two regions is at least two times higher than the rigidity of a more distal one of the at least two regions.

13. The redirector of claim 1, wherein an outer jacket of the shaft includes, proximal to the exposed portion of the external pull wire, three regions of stiffness increasing in the distal to proximal direction, wherein a rigidity of each of the three regions is at least two times higher than the rigidity of a distally adjacent one of the three regions.

14. The redirector of claim 1, wherein the shaft includes a first and second stiffness planes extending longitudinally along at least a portion of the shaft, the first and second stiffness planes oriented orthogonally to one another, wherein the shaft is stiffer along the second stiffness plane than the first stiffness plane.

15. The redirector of claim 14, wherein the shaft is at least one of the following: at least 50% stiffer along the second stiffness plane than the first stiffness plane or at least 55% stiffer along the second stiffness plane than the first stiffness plane.

16. The redirector of claim 14, wherein the shaft includes a reinforcing wire positioned along the second stiffness plane.

17. The redirector of claim 14, wherein the shaft includes a reinforcing wire positioned along the second stiffness plane.

18. The redirector of claim 1, wherein the internal pull wire and the external pull wire extend side-by-side through the proximal portion of the shaft.

19. A redirector positionable in a left ventricle, the redirector comprising:
an elongate shaft having a tubular lumen, the shaft having a proximal portion and a distal portion actively steerable between a generally straight position and a curved position;
an internal pull wire and an external pull wire directly adjacent to the internal pull wire, wherein the external pull wire extends internally through the proximal portion of the shaft and longitudinally along the exterior of the distal portion of the shaft, wherein when the shaft is in the curved position, the external pull wire locks the shaft in the curved position;
a return wire extending longitudinally through the shaft, the return wire extending parallel to, and positioned 180 degrees from, the internal and external pull wires,
first and second actuators each moveable in a proximal direction and a distal direction, the first actuator operatively associated with the internal and external pull wires and the second actuator operatively associated with the return wire, the first and second actuators operatively coupled such that first and second actuators are moveable simultaneously in opposite ones of the proximal and distal directions.

20. The redirector of claim 19 wherein when the shaft is locked by the external pull wire in the curved position, the shaft retains the shape of the curved position when a distal tip of the shaft is subjected to an axial force of at least one of the following: over 40N, over 50N, over 60N or over 70N.

21. The redirector of claim 19, wherein when the shaft is locked by the external pull wire in the curved position, the pull wire has an exposed length external to the shaft, and wherein the external pull wire substantially maintains the length of its exposed length when a distal tip of the shaft is subjected to an axial force of at least one of the following: over 40N, over 50N, over 60N, or over 70N.

22. The redirector of claim 19, wherein the elongate shaft in the curved position has a distal curve with an articulation angle A relative to the longitudinal axis of the proximal portion of the shaft when the proximal portion is positioned in a straight configuration, and wherein the angle A is in the range of 100-140 degrees.

23. The redirector of claim 19, wherein the internal pull wire and the external pull wire extend side-by-side through the proximal portion of the shaft.

* * * * *